US006492418B2

(12) United States Patent
Miller et al.

(10) Patent No.: US 6,492,418 B2
(45) Date of Patent: Dec. 10, 2002

(54) COMPOSITIONS CONTAINING A BENZAMIDE DISULFIDE DERIVATIVE FOR TREATING ALLERGIC DISEASES

(75) Inventors: Steven T. Miller, Arlington, TX (US); Mark R. Hellberg, Arlington, TX (US); Zixia Feng, Arlington, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/843,131

(22) Filed: Apr. 25, 2001

(65) Prior Publication Data

US 2002/0065281 A1 May 30, 2002

Related U.S. Application Data

(60) Provisional application No. 60/206,083, filed on May 19, 2000.

(51) Int. Cl.$^7$ ............................................. A61K 31/225
(52) U.S. Cl. ........................ 514/548; 514/616; 514/912
(58) Field of Search ................................. 514/548, 616, 514/912

(56) References Cited

U.S. PATENT DOCUMENTS

| | | | |
|---|---|---|---|
| 3,573,320 A | 3/1971 | Jansen | 260/305 |
| 3,663,616 A | 5/1972 | Grivas | 260/558 |
| 4,705,805 A | 11/1987 | Yamada et al. | 514/548 |
| 4,871,865 A | 10/1989 | Lever, Jr. et al. | 549/354 |
| 4,923,892 A | 5/1990 | Lever, Jr. et al. | 514/450 |
| 5,116,863 A | 5/1992 | Oshima et al. | 514/450 |
| 5,224,980 A | 7/1993 | Austin et al. | 514/231.8 |
| 5,315,009 A | 5/1994 | Austin et al. | 548/209 |
| 5,463,122 A | 10/1995 | Elslager et al. | 564/82 |
| 5,641,805 A | 6/1997 | Yanni et al. | 514/450 |
| 5,668,178 A | 9/1997 | Elslager et al. | 514/618 |
| 5,668,291 A | 9/1997 | Domagala et al. | 546/316 |
| 5,734,081 A | 3/1998 | Domagala et al. | 564/82 |
| 5,859,017 A | 1/1999 | Eiseman et al. | 514/263 |
| 5,929,114 A | 7/1999 | Domagala et al. | 514/562 |
| 6,001,555 A | 12/1999 | Henderson et al. | 435/5 |

FOREIGN PATENT DOCUMENTS

| | | |
|---|---|---|
| DE | 274220 A1 | 12/1989 |
| EP | 0 006 227 A | 1/1980 |
| JP | 09005926 | 10/1997 |
| JP | 10 316651 A | 12/1998 |
| WO | 97/38693 | 10/1997 |
| WO | WO 98/35937 | 8/1998 |

OTHER PUBLICATIONS

Boyer et al., "2,2'–Dithiobisbenzamides Derived from β–and γ–Amino Acids as HIV–1 Inhibitors Via Interaction with Nucleocapsid Protein NCp7: Synthesis and Structure Activity Relationship," Parke Davis 25$^{th}$ National Medicinal Chemistry Symposium, An Arbor Michigan, Jun. 18–22, 1996.

Domagala et al., "A New Class of Anti–HIV–1 Agents Targeted Toward the Nucleocapsid Protein NCp7: The 2,2'–Dithiobisbenzamides," *Bioorganic & Medicinal Chemistry*, vol. 5 (3), pp. 569–579 (1997).

Kim et al., "Inhibition of Histamine Release from Dispersed Human Lung and Tonsillar Mast Cells by Nicardipine and Nifedipine," *Br. J. Clin. Pharmacol.*, vol. 19(5), pp. 631–638 (1985).

Rice et al., "Inhibitors of HIV Nucleocapsid Protein Zinc Fingers as Candidates for the Treatment of AIDS," *Science*, vol. 270, pp. 1194–1197 (1995).

Rotmistrov et al., "Antimicrobial Properties of Phenyl Disulfide Derivatives," *Mikrobiol. Zh.*, vol. 30(2); pp. 153–157 (1968) (Abstract only).

Tanizaki et al., "Actions and cross–reactivity of antiallergic agents and a calcium channel antagonist on rat peritoneal mast cells. Difference in the action mechanisms and cross–reactivity among the agents," *Agents Actions* vol. 37, pp. 8–15 (1992).

Tanizaki et al., Inhibitory effect of nefedipine and cromolyn sodium on skin reactions and $^{45}$Ca uptake and histamine release in rat mast cells induced by various stimulating agents, *Int. Arches Allergy Apple. Immune.*, vol. 72, pp. 102–109 (1983).

Yamada et al., "Evidence that KF4939, a new anti–platelet agent, inhibits phospholipase activation in rabbit platelets: different aspects from cyclic AMP increasing agents and calmodulin antagonist," *Archives Internationales de Pharmacodynamie et de Therapie*, vol. 268(1), pp. 141–154 (1984).

Yamada et al., "Inhibition of platelet aggregation by a new agent, 2,2'–dithiobis–(N–2–hydroxypropyl benzamide) (KF4939)," *Thrombosis Research*, vol. 29(2), pp. 197–206 (1983).

Yamada et al., "Inhibition of thromboxane A2–induced vasocontraction by KF4939, a new anti–platelet agent, in rabbit mesenteric and dog coronary arteries," *Japanese Journal of Pharmacology*, vol. 36(3), pp. 283–290 (1984).

Yamada et al., "Involvement of disulfide–sulfhydryl interaction in anti–platelet action of KF4939," *Thrombosis Research*, vol. 38(1), pp. 61–69 (1985).

Yamada et al., "KF4939, a new anti–platelet agent, inhibits activation of phospholipase C and A2 in rabbit platelets," *Japanese Journal of Pharmacology*, vol. 39(1), pp. 108–111 (1985).

MDL Information Systems, Inc. Database "Available Chemicals Directory," 1999 (2), commercially available 2,2'Dithiodianiline derivatives.

(List continued on next page.)

*Primary Examiner*—Zohreh Fay
(74) *Attorney, Agent, or Firm*—Patrick M. Ryan

(57) ABSTRACT

Methods and compositions for preventing or treating allergic diseases of the eye, nose, skin, ear, gastrointestinal tract, airways or lung and preventing or treating manifestations of systemic mastocytosis are disclosed. The compositions contain a mast cell stabilizing disulfide derivative as an active ingredient.

7 Claims, No Drawings

OTHER PUBLICATIONS

SciFinder database record for Registry No. 122686–59–3, 2–Propenamide, N,N –(dithiodi–2, 1–phenylene)bis2–methyl–(9CI).

Borgna et al., "Diacilaminodiefenildisolfuri ad aziione inibente la reazione di Hill," *Farmaco, Edizone Scientifica*, vol. 29(2), pp. 120–128 (1974).

Rice et al., "Evaluation of selected chemotypes in coupled cellular and molecular target–based screens identifies novel HIV–1 zinc finger inhibitors," *J. or Medicinal Chemistry*, vol. 39(19), pp. 3606–3616 (1996).

Sellstedt et al., "Oxanilic acids, a new series of orally active antiallergic agents," *J. of Medicinal Chemistry*, vol. 18(9), pp. 926–933 (1975).

Simov et al., "Über die Wechselwirkung zwischen Benzthiazolon und Aminen," *Comptes Rendus De L'Academie Bulgare Des Sciences*, vol. 21(9), pp, 881–884 (1968).

Bertamino, R. "Results with an association of O.D. 507 (diphenyldisulfide 2,2' dicarboxylic acid dibutylamide) and triamcinolone in 84 cases of dermatosis. L. Associaziione O.D. 507 E Triamcinolone in Dermatosi Varie," *G. Ital. Derm. Minerva Derm.*, vol. 108(12), pp. 641–646 (1973).

Favari et al., "Cellular Toxicity of N–Substituted 2,2'–Dicarboxamidodiphenyldisulph Ides with High Antimicrobial Activity," *Pharmacological Research, Academic Press*, vol. 40(5); pp. 429–434 (1999).

COMPOSITIONS CONTAINING A BENZAMIDE DISULFIDE DERIVATIVE FOR TREATING ALLERGIC DISEASES

This application claims priority from co-pending U.S. Provisional Application, U.S. Ser. No. 60/206,083, filed May 19, 2000.

BACKGROUND OF THE INVENTION

1. Field of the Invention

The present invention relates to the treatment of allergic diseases. More particularly, the present invention relates to therapeutic and prophylactic use of certain disulfide derivatives for treating or preventing allergic diseases.

2. Description of the Related Art

Antihistamines and mast cell stabilizers are two types of drugs currently used topically to treat allergic diseases. Antihistamine drugs are used to interrupt the allergic effects that histamine causes after it has been released from a mast cell. Many topical antihistamine drugs are marketed. For example, emedastine difumarate and levocabastine hydrochloride are available for ocular allergies (see *Ophthalmic Drug Facts* 1999, Facts and Comparisons, St. Louis, Mo., pp. 59–80).

Mast cell stabilizers prevent mast cells from "degranulating" or releasing histamine and other components or "mediators" during an allergic reaction. Examples of ophthalmic drugs marketed as mast cell stabilizers include olopatadine (see U.S. Pat. No. 5,641,805) and cromolyn sodium.

U.S. Pat. No. 4,705,805 discloses certain disulfide derivatives that are useful as anti-thrombotic agents. The disulfide derivatives suppress blood platelet aggregation. The '705 patent does not disclose the use of disulfide derivatives in the topical treatment of allergic diseases of the eye or nose.

SUMMARY OF THE INVENTION

The present invention provides methods for preventing or treating allergic diseases of the eye, nose, skin, ear, gastrointestinal tract, airways or lung. The methods may also be used to treat manifestations of systemic mastocytosis. The methods of the present invention comprise topically or systemically administering to a patient a mast cell stabilizing disulfide derivative of the formula

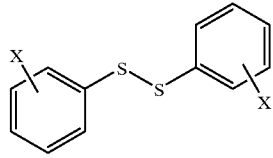

(I)

wherein X is —C(=O)—N(—$R^1$)—R;

R and $R^1$ are independently H; (un)substituted phenyl; (un)substituted benzyl; or $C_1$–$C_8$ alkyl or alkenyl, optionally substituted with or terminated by OH, $OR^2$, $NR^3R^4$; $C_4$–$C_7$ cycloalkyl, (un)substituted aryl, or (un)substituted 5–7 membered heterocyclic ring; where optional substituents are selected from the group consisting of $C_1$–$C_6$ alkyl or alkoxy; halogen; OH; CN; $CF_3$; $NO_2$; and $CO_2R^2$;

$R^2$ is $C_1$–$C_3$ alkyl; and $R^3$ and $R^4$ are independently H; benzyl; $C_1$–$C_8$ alkyl or alkenyl; $C_4$–$C_7$ cycloalkyl; (un)substituted aryl; or (un) substituted 5–7 membered heterocyclic ring; wherein optional substituents are selected from the group consisting of $C_1$–$C_6$ alkyl or alkoxy; halogen; OH; CN; $CF_3$; $NO_2$; and $CO_2R^2$.

The present invention is also directed toward topically or systemically administrable compositions for treating or preventing allergic diseases of the eye, nose, skin, ear, gastrointestinal tract, airways or lung and treating or preventing manifestations of systemic mastocytosis, wherein the compositions comprise a disulfide derivative of formula (I).

DETAILED DESCRIPTION OF THE INVENTION

The disulfide derivatives of formula (I) are known or are commercially available from sources such as Aldrich Chemical Company (Sigma Aldrich Library of Rare Chemicals) in Milwaukee, Wis. and Maybridge Chemical Company Ltd. in the U.K or can be made using known techniques, such as those described in Domagala J M et al. *Biorganic and Medicinal Chemistry* volume 5 No. 3 pages 569–79 (1997), and U.S. Pat. No. 4,705,805 (Yamotsu K. et al., 1987). The entire contents of both of these references are incorporated by reference.

Preferred compounds of formula (I) are those having the X substituents in the ortho position.

Most preferred are compounds wherein R and $R^1$ independently=H; $C_1$–$C_5$ alkyl or alkenyl, optionally substituted with or terminated by OH, $OR^2$ $NR^3R^4$, $C_4$–$C_7$ cycloalkyl, (un)substituted aryl, or (un)substituted 5–7 membered heterocyclic ring, wherein optional substituents are selected from the group consisting of $C_1$–$C_6$ alkyl or alkoxy; halogen; OH; CN; $CF_3$; $NO_2$; and $CO_2R^2$.

Compounds of formula (I) may be administered topically (i.e., local, organ-specific delivery) or systemically by means of conventional topical or systemic formulations, such as solutions, suspensions or gels for the eye and ear; nasal sprays or mists for the nose; metered dose inhalers for the lung; solutions, gels, creams or lotions for the skin; oral dosage forms including tablets or syrups for the gastrointestinal tract; and parenteral dosage forms including injectable formulations. The concentration of the compound of formula (I) in the formulations of the present invention will depend on the selected route of administration and dosage form. The concentration of the compound of formula (I) in topically administrable formulations will generally be about 0.00001 to 5 wt. %. For systemically administrable dosage forms, the concentration of the compound of formula (I) will generally range from about 10 mg to 1000 mg.

The preferred formulation for topical ophthalmic administration is a solution intended to be administered as eye drops. For solutions intended for topical administration to the eye, the concentration of the compound of formula (I) is preferably 0.0001 to 0.2 wt. %, and most preferably from about 0.0001 to 0.01 wt. %. The topical compositions of the present invention are prepared according to conventional techniques and contain conventional excipients in addition to one or more compounds of formula (I). A general method of preparing eye drop compositions is described below:

One or more compounds of formula (I) and a tonicity-adjusting agent are added to sterilized purified water and if desired or required, one or more excipients. The tonicity-adjusting agent is present in an amount sufficient to cause the final composition to have an ophthalmically acceptable osmolality (generally about 150–450 mOsm, preferably 250–350 mOsm). Conventional excipients include preservatives, buffering agents, chelating agents or stabilizers, viscosity-enhancing agents and others. The chosen ingredients are mixed until homogeneous. After the solution is mixed, pH is adjusted (typically with NaOH or HCl) to be within a range suitable for topical ophthalmic use, preferably within the range of 4.5 to 8.

Many ophthalmically acceptable excipients are known, including, for example, sodium chloride, mannitol, glycerin or the like as a tonicity-adjusting agent; benzalkonium chloride, polyquaternium-1 or the like as a preservative; sodium hydrogenphosphate, sodium dihydrogenphosphate, boric acid or the like as a buffering agent; edetate disodium or the like as a chelating agent or stabilizer; polyvinyl alcohol, polyvinyl pyrrolidone, polyacrylic acid, polysaccharide or the like as a viscosity-enhancing agent; and sodium hydroxide, hydrochloric acid or the like as a pH controller.

If required or desired, other drugs can be combined with the disulfide derivatives of formula (I), including, but not limited to, antihistaminic agents, anti-inflammatory agents (steroidal and non-steroidal), and decongestants. Suitable antihistaminic agents include emedastine, mapinastine, epinastine, levocabastine, loratadine, desloratadine, ketotifen, azelastine, cetirazine, and fexofenadine. The preferred antihistaminic agent for ophthalmic use is emedastine, which is generally included in topically administrable compositions at a concentration of 0.001–0.1 wt. %, preferably 0.05 wt. %. Suitable anti-inflammatory agents include mometasone, fluticasone, dexamethasone, prednisolone, hydrocortisone, rimexolone and loteprednol. Suitable decongestants include oxymetazoline, naphazoline, tetrahydrozoline, xylometazoline, propylhexedrine, ethyinorepinephrine, pseudoephedrine, and phenylpropanolamine.

According to the present invention, the disulfide derivatives of formula (I) are useful for preventing and treating ophthalmic allergic disorders, including allergic conjunctivitis, vernal conjunctivitis, vernal keratoconjunctivitis, and giant papillary conjunctivitis; nasal allergic disorders, including allergic rhinitis and sinusitis; otic allergic disorders, including eustachian tube itching; allergic disorders of the upper and lower airways, including intrinsic and extrinsic asthma; allergic disorders of the skin, including dermatitis, eczema and urticaria; allergic disorders of the gastrointestinal tract, including systemic anaphylaxis resulting from ingestion of allergen and iatrogenic anaphylaxis caused by contrast agents used during diagnostic imaging procedures; and manifestations of systemic mastocytosis including hypotension.

The following examples are intended to be illustrative but not limiting.

EXAMPLE 1

Topical Ophthalmic Solution Formulation

| Ingredient | Concentration (wt. %) |
|---|---|
| Compound of formula (I) | 0.0001 to 0.2 |
| Dibasic Sodium Phosphate (Anhydrous) | 0.5 |
| Sodium Chloride | 0.65 |
| Benzalkonium Chloride | 0.01 |
| NaOH/HCl | q.s. pH 6–8 |
| Purified Water | q.s. 100 |

EXAMPLE 2

Topical Ophthalmic Gel Formulation

| Ingredient | Concentration (wt. %) |
|---|---|
| Compound of formula (I) | 0.0001 to 0.2 |
| Carbopol 974 P | 0.8 |
| Edetate Disodium | 0.01 |
| Polysorbate 80 | 0.05 |
| Benzalkonium Chloride | 0.01 |
| NaOH/HCl | q.s. pH 6–8 |
| Water for Injection | q.s. 100 |

EXAMPLE 3

Synthesis of 2, 2-dithio-bis(N-3-morpholinopropyl-benzamide) (II)

2,2-Dithiodibenzoic acid chloride (1.5 g, 4.37 mmol) was dissolved in 10 ml of dioxane and cooled to 10° C. To this solution, 4-(3-aminopropyl)morpholine (1.3 ml, 8.74 mmol) was added slowly under nitrogen. The resulting mixture was stirred at 10° C. for 1 hr and then at 70° C. for 2 hr. After cooling, the solids were filtered off. The filtrate was placed at room temperature. Yellowish solids precipitated and were filtered. The crude product was recrystallized with ethanol/ethyl ether (1:3), giving 0.80 g of white product (II).

$^1$H NMR (CDCl$_3$) δ8.04–7.18 (m, 8H), 3.73–3.54 (m, 12H), 2.60–2.39 (m, 12H), 1.87–1.80 (m, 4H). $^{13}$C NMR (CDCl$_3$) δ167.63 (C=O), 137.32 (C), 134.23 (C), 131.07 (CH), 127.25 (CH), 127.17 (CH), 125.92 (CH), 66.91 (CH$_2$), 58.49 (CH$_2$), 53.74 (CH$_2$), 40.35 (CH$_2$), 24.21 (CH$_2$). Analysis calculated for C$_{28}$H$_{38}$O$_4$N$_4$S$_2$ requires: C, 60.19; H, 6.85; N, 10.03%. Found: C, 60.15; H, 6.82; N, 9.96%.

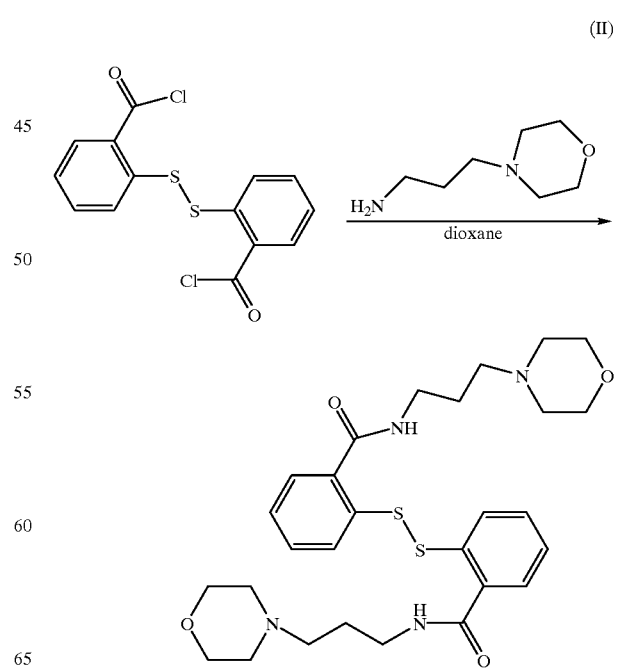

EXAMPLE 4

Mast Cell Activity

Preparation of Cell Suspension

Methods detailing preparation of mono-dispersed HCTMC and mediator release studies with these cells have been described (U.S. Pat. No. 5,360,720 and Miller et al, Ocular Immunology and Inflammation, 4(1):39–49 (1996)). Briefly, human conjunctival tissue mast cells were isolated from post-mortem tissue donors obtained within 8 hours of death by various eye banks and transported in Dexsol® corneal preservation medium, or equivalent. Tissues were enzymatically digested by repeated exposure (30 min. at 37° C.) to collagenase and hyaluronidase (2× with 200 U each/gram tissue, then 2–4 × with 2000 U each/gram tissue) in Tyrode's buffer containing 0.1% gelatin. (Tyrode's buffer (in mM): 137 NaCl, 2.7 KCl, 0.35 $NaH_2PO4$, 1.8 $CaCl_2$, 0.98 $MgCl_2$, 11.9 $NaHCO_3$, and 5.5 glucose). Each digestion mixture was filtered over Nitex® cloth (100 μm mesh, Tetko, Briarcliff Manor, N.Y.) and washed with an equal volume of buffer. Filtrates were centrifuged at 825×g (7 min). Pellets were resuspended in buffer then combined for enrichment over a 1.058 g/L Percoll® cushion. The enriched pellet was washed, resuspended in supplemented RPMI 1640 medium and incubated at 37° C. to equilibrate.

Histamine Release Studies

Cells were harvested from the culture plate and counted for viability (trypan blue exclusion) and mast cell number (toluidine blue O). Mast cells (5000/tube; 1 mL final volume) were challenged (37° C.) for 15 min with goat-anti-human IgE (10 μg/mL) following treatment (15 minutes; 37° C.) with test drug or Tyrode's buffer. Total and non-specific release controls were exposed to 0.1% Triton X-100 and goat IgG (10 μg/mL), respectively. The reaction was terminated by centrifugation (500×g, 4° C., 10 min). Supernatants were stored at −20° C. until analyzed for histamine content by RIA (Beckman Coulter, Chicago, Ill.).

Preparation of Test Drug Solutions

All test drugs were made to solution immediately prior to use. Each was dissolved in DMSO at 10 mM or greater concentration and then diluted in Tyrode's buffer containing 0.1% gelatin over the concentration for evaluation.

Data Analysis

Inhibition of histamine release was determined by direct comparison of with anti-IgE challenged mast cells using Dunnett's t-test (Dunnett, "A multiple comparison procedure for comparing treatments with a control", J. Amer. Stat. Assoc. (1955), 50:1096–1121). An IC50 value (the concentration at which the test compound inhibits histamine release at a level of 50% compared to the positive control) was determined by 4-parameter logistic fitting using the Levenburg-Marquardt algorithm or by linear regression. The results are reported in Table 1.

TABLE 1

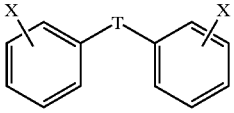

| COMPOUND NO. | T | X | MOLSTRUCTURE | IC50(nM) |
|---|---|---|---|---|
| 1 | S—S | 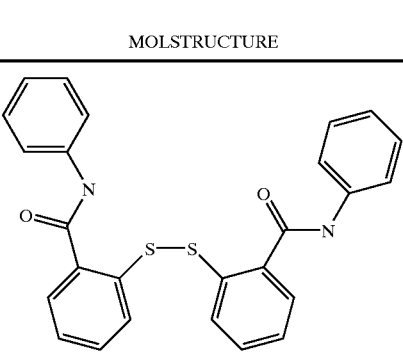 | 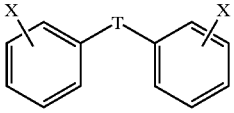 | 39 |
| 2 | S—S | 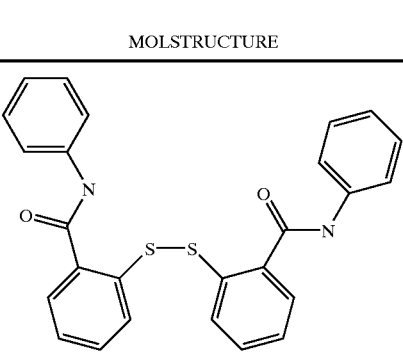 |  | 78<br>199<br>39<br>[105] |

TABLE 1-continued
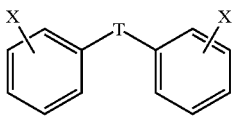
| COMPOUND NO. | T | X | MOLSTRUCTURE | IC50(nM) |
|---|---|---|---|---|
| 3 | S—S | 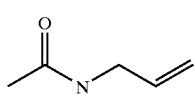 | 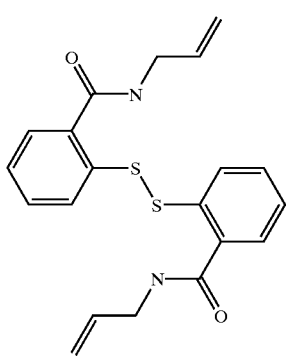 | 21<br>388<br>231<br>121<br>141<br>9<br>128<br>[148] |
| 4 | S—S | 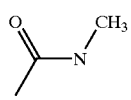 | 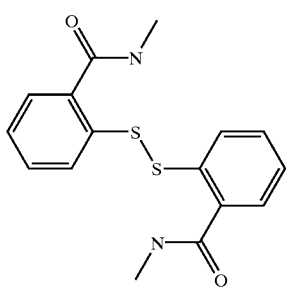 | 39<br>69<br>1700<br>140<br>95<br>409<br>149<br>66<br>60<br>90<br>[282] |
| 5 | S—S | 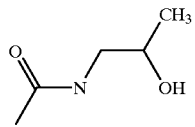 | 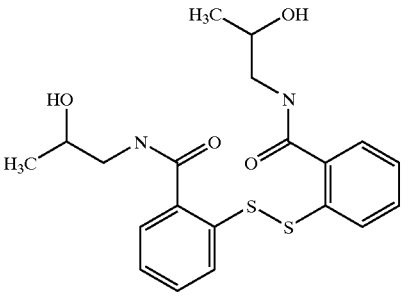 | 107<br>219<br>229<br>84<br>71<br>[122] |
| 6 | S—S | 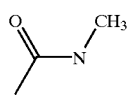<br>meta displacement | 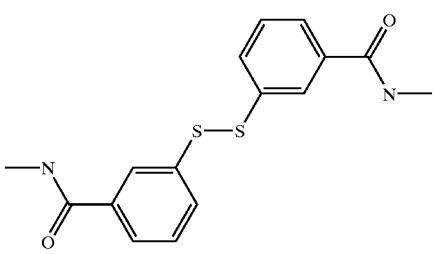 | 402<br>222<br>[312] |

The data shown in Table 1 indicate that the compounds of formula (I) potently inhibit histamine release from human conjunctival mast cells in an in vitro model of allergic conjunctivitis.

EXAMPLE 5

Topical Ophthalmic Solution Formulation

| Ingredient | Concentration (wt. %) |
|---|---|
| Compound of formula (I) | 0.0001 to 0.2 |
| Emedastine | 0.001 to 0.1 |
| Dibasic Sodium Phosphate (Anhydrous) | 0.5 |
| Sodium Chloride | 0.65 |
| Benzalkonium Chloride | 0.01 |
| NaOH/HCl | q.s. pH 6–8 |
| Purified Water | q.s. 100 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for prophylactically treating an allergic disease of the eye, nose, skin, ear or lung in a patient suceptible to the same or treating an allergic disease of the eye, nose, skin, ear or lung in a patient experiencing the same comprising topically administering to the patient a composition comprising a disulfide derivative of the formula

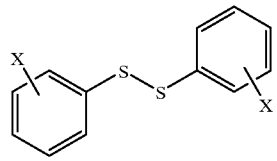

wherein X is —C(=O)—N(—R$^1$)—R;

R and R$^1$ are independently H; (un)substituted phenyl; (un)substituted benzyl; or C$_1$–C$_8$ alkyl or alkenyl, optionally substituted with or terminated by OH, OR$^2$, NR$^3$R$^4$; C$_4$–C$_7$ cycloalkyl, (un)substituted aryl, or (un)substituted 5–7 membered heterocyclic ring; where optional substituents are selected from the group consisting of C$_1$–C$_6$ alkyl or alkoxy; halogen; OH; CN; CF$_3$; NO$_2$; and CO$_2$R$^2$;

R$^2$ is C$_1$–C$_3$ alkyl; and

R$^3$ and R$^4$ are independently H; benzyl; C$_1$–C$_8$ alkyl or alkenyl; C$_4$–C$_7$ cycloalkyl; (un)substituted aryl; or (un)substituted 5–7 membered heterocyclic ring; wherein optional substituents are selected from the group consisting of C$_1$–C$_6$ alkyl or alkoxy; halogen; OH; CN; CF$_3$; NO$_2$; and CO$_2$R$^2$.

2. The method of claim 1 wherein the X substituents are in the ortho position.

3. The method of claim 2 wherein R and R$^1$ independently=H; C$_1$–C$_5$ alkyl or alkenyl, optionally substituted with or terminated by OH, OR$^2$, NR$^3$R$^4$, C$_4$–C$_7$ cycloalkyl, (un)substituted aryl, or (un)substituted 5–7 membered heterocyclic ring, wherein optional substituents are selected from the group consisting of C$_1$–C$_6$ alkyl or alkoxy; halogen; OH; CN; CF$_3$; NO$_2$; and CO$_2$R$^2$.

4. The method of claim 3 wherein X is selected from the group consisting of

—C(=O)—NHC$_6$H$_5$;  —C(=O)—NHCH$_2$CH=CH$_2$;
—C(=O)—NHCH$_3$; and

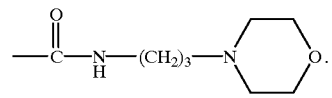

5. The method of claim 1 wherein the disulfide derivative is administered to the patient in a composition containing the disulfide derivative in an amount from about 0.00001 to 5 wt. %.

6. The method of claim 5 wherein the disulfide derivative is present in an amount from about 0.0001 to 0.2 wt. %.

7. The method of claim 6 wherein the disulfide derivative is present in an amount from about 0.0001 to 0.01 wt. %.

* * * * *